United States Patent [19]

Clincke et al.

[11] Patent Number: 5,691,201
[45] Date of Patent: Nov. 25, 1997

[54] USE OF SABELUZOLE IN CHRONIC NEURODEGENERATIVE DISEASES

[75] Inventors: Gilbert Henri Camiel Clincke, Vosselaar; Luc Remi Mathilde Tritsmans, Vlimmeren; Hugo Alfons Gabriel Geerts, Berchem, all of Belgium

[73] Assignee: Janssen Pharmaceutica, N.V., Beerse, Belgium

[21] Appl. No.: 537,704

[22] PCT Filed: Apr. 13, 1994

[86] PCT No.: PCT/EP94/01177

§ 371 Date: Oct. 11, 1995

§ 102(e) Date: Oct. 11, 1995

[87] PCT Pub. No.: WO94/25029

PCT Pub. Date: Nov. 10, 1994

[30] Foreign Application Priority Data

Apr. 26, 1993 [EP] European Pat. Off. ............ 93 201 193
May 18, 1993 [EP] European Pat. Off. ............ 93 201 411

[51] Int. Cl.$^6$ .................................................... C12N 5/00
[52] U.S. Cl. .................................... 435/368; 435/325
[58] Field of Search ............................. 435/325, 368

[56] References Cited

FOREIGN PATENT DOCUMENTS

WO92/03137  3/1992  WIPO.

OTHER PUBLICATIONS

Geerts et al., "Sabeluzole, a Memory–Enhancing Molecule, Increases Fast Axonal Transport in Neuronal Cell Cultures", Exp. Neurology 117, 36–43 (1992).

Robbins, "Arresting memory decline", Nature, vol. 336, pp. 207–208, 17 Nov. 1988.

De Deyn et al., "Single–dose and steady–state pharmacokinetics of sabeluzole in senile dementia of Alzheimer type patients", Eur. J. Clinical Pharmacology, vol. 43, No. 6, pp. 661–662, 1992.

Werbrouck et al., "Comparison of the In Vivo Pharmacological Profiles of Sabeluzole and Its Enantiomers", Drug Development Research 24:41–51 (1991).

Maloteaux et al., "Progress in Research and Treatment in Regard to Alzheimer's Disease", Louvain Medical, vol. 112(4), pp. 283–288, 1993 [original and translation].

Clincke et al., "R 58 736, a Novel Antihypoxic Drug Improves Memory in Rats", Drug Development Research 8:381–385 (1986).

Clincke et al., "Sabeluzole (R 58 735) increases consistent retrieval during serial learning and relearning of nonsense syllables", Psychopharmacology (1988) 96:309–310.

Tritsmans et al., "Memory Study with Sabeluzole in a Population with a Mean Age of 85 Years: A Pilot Experiment", Current Therapeutic Research, vol. 44, No. 6, Dec. 1988, pp. 966–974.

Geerts et al., "Sabeluzole accelerates neurite outgrowth in different neuronal cell lines", Restorative Neurology and Neuroscience, 4 (1992) 21–32.

Primary Examiner—John W. Rollins
Attorney, Agent, or Firm—Charles J. Metz

[57] ABSTRACT

The present invention is concerned with the use of sabeluzole for the manufacture of a medicament for the treatment of patients suffering from chronic neuro-degenerative diseases such as dementia of the Alzheimer type (DAT) or Alzheimer's disease, amyotrophic lateral sclerosis (ALS), dementia associated with Parkinson's disease and related diseases which are characterized by progressive dementia.

1 Claim, No Drawings

USE OF SABELUZOLE IN CHRONIC NEURODEGENERATIVE DISEASES

CROSS-REFERENCE TO RELATED APPLICATIONS

This application is based upon PCT application Ser. No. PCT/EP 94/01177, filed Apr. 13, 1994, which claims priority from European Patent Application Serial Nos. 93.201.193.5, filed on Apr. 26, 1993, and 93.201.411.1, filed on May 18, 1993.

The present invention is concerned with the use of sabeluzole for the manufacture of a medicament for the treatment of patients suffering from chronic neuro-degenerative diseases such as dementia of the Alzheimer type (DAT) or Alzheimer's disease, amyotrophic lateral sclerosis (ALS), dementia associated with Parkinson's disease and other central nervous system diseases which are characterized by progressive dementia. Said treatment comprises the administration of sabeluzole in an amount effective in improving, halting, retarding or palliating the course and/or effects of said chronic neurodegenerative diseases. The invention also concerns a method of treating patients suffering from chronic neurodegenerative diseases by administering to said patients an amount of sabeluzole effective in improving, halting, retarding or palliating the course and/or effects of said neurodegenerative diseases. Further there are provided a method of attenuating neuronal cell death in neuronal cells in contact with factors inducing the expression of epitopes associated with aberrantly phosphorylated tau-protein, and a method of inhibiting the formation in neuronal cells of neurofibrillary tangles, which consist mainly of aberrantly phosphorylated tau-protein, said methods comprising contacting said cells with an amount of sabeluzole effective in attenuating said cell death, and in inhibiting the formation of said tangles. The invention also relates to a method of inducing in neuronal cells the expression of epitopes associated with aberrantly phosphorylated tau-protein, which method comprises contacting said cells with a medium conditioned from serum-starved cells for several days and having acquired cytotoxic activity. The invention also concerns a novel polymorph of sabeluzole having improved solubility properties, compositions comprising this novel polymorph and methods for preparing said polymorph and compositions.

In U.S. Pat. No. 4,861,785 there are described compounds having antihypoxic and antianoxic properties useful in indications such as shock, cardiac arrest and severe blood loss. Among these compounds features 4-(2-benzothiazolylmethylamino-α-[(4-fluoro-phenoxy)methyl]-1-piperidineethanol, mp. 101.7 ° C., which is generically known as sabeluzole. Subsequent investigations with this compound have shown it to have positive effects on adaptive learning behaviour in animals (Drug Dev. Res., 8, 381–385, 1986) and on memory in humans with suboptimal memory functions (Psychopharmacology, 96, 309–310, 1988; Curr. Ther. Res., 44, 966–974, 1988). The ability of sabeluzole to increase significantly fast axonal transport of submicrometer vesicles in neuronal cells is known from Experimental Neurology, 117, 36–43, 1992. Its accelerating effect on neurite outgrowth is described in Restorative Neurol. Neurosci., 4, 24–32, 1992.

Chronic neurodegenerative diseases are currently the main cause of progressive dementia in elderly people. Among these diseases, dementia of the Alzheimer type (DAT) or Alzheimer's disease is the most prevalent and is estimated to account for about 50% of all severe cases of dementia. Other forms of dementia, inter alia multi-infarct dementia which is due to damage to the nervous system following stroke or brain injury are slightly less common. However, these disorders are often complicated by chronic neurodegenerative diseases. Progressive dementia is characterized by impaired memory, language and visuo-spatial skills and behaviour. The debilitating changes occur over a long term ranging from six up to twenty or more years. Usually, between seven to ten years following onset of the symptoms the patient dies in mental oblivion. Neuropathological features characterizing the brain of people afflicted with Alzheimer's disease are:

- scattered congophilic aggregations of amyloid (β) protein deposits in the brain parenchyma and the wall of the leptomeningeal blood vessels;
- formation of and collections of twisted filaments known as neurofibrillary tangles which accumulate within neurons and in the brain parenchyma;
- formation of and collection of the twisted filaments around parenchymatous congophilic aggregations of amyloid (β) protein deposits, called neuritic or senile plaques;
- significant loss of neurons in the regions of the brain essential for memory and cognition with endings in the cerebral cortex;
- reduction in the amount of neurotransmitters (especially acetylcholine) i.e. multi-neurotransmitter deficit disorder; and
- progress so pervasive that all cortical areas are finally involved.

Currently the most direct link between signs and symptoms of Alzheimer's disease and observable neuropathology is the occurence of amyloid and neurofibrilllary tangles. The loss of cells and neurotransmitters appears to be a secondary event in pathogenesis rather than a cause.

Contemporary treatment is mainly symptomatic and includes, among others, neurotransmitter replacement which is mainly focused on the substitution of cholinergic loss. In general, the current therapies offer little improvement in human cognitive performance and do not retard, let alone halt or reverse the inexorable course of chronic neurodegenerative diseases. Moreover the present drugs suffer from displaying unwanted side-effects such as depression (physostigmine) and hepatotoxicity (tacrine).

The present invention is concerned with the use of sabeluzole for the manufacture of a medicament for the treatment of patients suffering from chronic neuro-degenerative diseases such as dementia of the Alzheimer type (DAT) or Alzheimer's disease, amyotrophic lateral sclerosis (ALS), dementia associated with Parkinson's disease and other central nervous system diseases which are characterized by progressive dementia.

Unexpectedly, clinical trials have shown that chronic treatment of Alzheimer patients with sabeluzole is capable of retarding, halting and even reversing the course and/or the effects of the disease of these patients. The clinical data which are more fully described and discussed in the clinical examples, show that there is not merely a symptomatic improvement of the patients, but that the progression of the disease is actually retarded and that a number of cognitive items are significantly preserved when compared to placebo controls. Chronic treatment, as evidenced by the results described in the clinical examples presented hereinafter, comprises administering to the patients an amount of 5, 10 or 20 mg b.i.d. or 10, 20 or 40 mg o.d. for the duration of at least 6 to 12 months. The twice-a-day administration ensures that effective plasma levels are attained continuously throughout the day, although combination to a once daily dose or division of the daily amount into three four or more subdoses obviously also would yield a similar result. The optimal dose regime, allowing for individual responses, would be from about 2 mg b.i.d. to about 10 mg b.i.d. and most preferably would be about 5 mg b.i.d.

Add-on therapies of sabeluzole with those medicaments that give symptomatic improvement, in particular those that affect neurotransmitters, e.g. tacrine and velnactine obviously may be of further benefit to the patients and may even yield synergistic results on particular neuropathological features and cognitive items assessed in the Alzheimer's Disease Assessment Scale (ADAS). As such these combinations of sabeluzole with tacrine and velnacrine are obviously intended to be included within the present invention. Therapeutic intervention at different stages of the disease is likely to yield qualitatively different results: if intervention occurs in an early stage, improving, halting or retarding of the disease process can be attained. In those patients where a genetic defect has been established, palliation of the effects can be obtained.

Corroborative evidence for the utility of sabeluzole in the treatment of patients suffering from for example dementia of the Alzheimer type has also been found in biochemical investigations using a novel testing system that should prove a useful model for Alzheimer's disease.

As mentioned hereinabove the most direct link between chronic neurodegenerative diseases such as Alzheimer's disease, and observable neuropathology presently is the occurrence of neurofibrillary tangles in neuronal cells. These tangles consist mainly of aberrantly phosphorylated tau-protein, which is a microtubule-associated protein. Its normal function is to stabilize the microtubule system. In the disease, modification of tau-protein is probably gradual, starting from pure dissociation between tau-protein and microtubuli, thus unmasking Alz-50 epitopes, and via clear pathological phosphorylation at serine residues at 199, 202 (which can conveniently be monitored with AT-8 antibody as described by Mercken; Acta Neuropathologica 84, 265–272 (1992)) and finally leading to paired helical filament structures. AT-8 reactivity of isolates of tau-protein can be shown using art-known immunocyto-chemistry methods or in Western Blots. Unexpectedly, it has now been found possible to induce in neuronal cells (e.g. human TR 14 and IMR-32 neuroblastoma cells) the expression of the tell-tale epitopes associated with aberrantly phosphorylated tau-protein. The method comprises culturing said cells at high confluency and in low serum conditions for a few days without changing the medium. Tau-protein isolated from these serum-starved and glucose deprived cells gives a clear AT-8 positive band on Western Blots which is shifted slightly upwards with regard to normal tau-protein, which can conveniently be stained with Tau-1 antibody, and which is alkaline phosphatase-dependent (i.e. upon treatment of the isolates with alkaline phosphatase, the AT-8 reactivity disappears and the bands reappear at a lower MW as indicated by the Tau-1 antibody). These observations are in complete register with the behaviour of AT-8 on Alzheimer brain autopsies. More importantly, incubation of freshly seeded neuronal cells at low confluency with medium obtained from the serum-starved, glucose deprived cells (hereinafter medium conditioned from serum-starved cells), induced readily observed anti-AT-8 immunocytochemistry over a period of 5 to 6 days. These data suggest that a soluble factor confers AT-8 immunoreactivity to neuronal cells cultures. The appearance of AT-8 immunoreactivity further is correlated with cytotoxicity, and in neurites of TR 14 cells with the occurrence of axonal constriction sites, where accumulation of moving vesicles is observed probably because of a deficient function of the microtubule system. In summary, the invention thus also concerns a method of inducing in neuronal cells the expression of epitopes associated with aberrantly phosphorylated tau-protein, which method comprises contacting said cells with a medium conditioned from serum-starved cells for several days and having acquired cytotoxic activity.

The above described method is deemed to be a useful tool in the screening of anti-Alzheimer drugs as it yields results with sabeluzole that correlate well with the clinical evidence. Indeed, when IMR-32 cells are incubated for 3 days with medium conditioned from 10-day serum-starved cells, sabeluzole can be shown to attenuate neurotoxicity (neuronal cell death) in a limited dosis range with maximum protection at about 0.1 µM. Thus, the invention provides a method of attenuating neuronal cell death in neuronal cells in contact with factors inducing the expression of epitopes associated with aberrantly phosphorylated tau-protein, and a method of inhibiting the formation in neuronal cells of neurofibrillary tangles, which consist mainly of aberrantly phosphorylated tau-protein carrying Alz 50 and AT-8 epitopes, said methods comprising contacting said cells with an amount of sabeluzole effective in attenuating said cell death.

It is advantageous to use a micronized form of sabeluzole, in particular material having an average particle size of less than 100 microns, preferably less than 75 microns, and in particular having a mean particle size of not more than 15 microns. The micronized form of sabeluzole has the advantage of dissolving better and more rapidly due to its high surface area. Micronized forms of sabeluzole can be prepared by micronization techniques known in the art, e.g. by milling in appropriate mills and sieving through appropriate sieves.

A new polymorph of the compound sabeluzole having advantageous properties has been identified. The higher melting polymorph I is the prior known form of sabeluzole (mp. 101.7° C., maximum 105.3° C., heat of fusion=99.6 J/g) and can be distinguished easily by its DSC characteristics from the novel, lower melting polymorph II (mp. 88.9° C., maximum 91.6° C., heat of fusion 84.2 J/g). X-ray diffraction analysis has confirmed the existence of the two polymorphs. Polymorph II is metastabile and considerably more rapidly dissolving than polymorph I, especially at mildly acidic pH values such as pH 4.5. This is of particular benefit because it is a pH value that is quite normal for the gastric contents of elderly patients and thus ensures that polymorph II will be resorbed without problems in these patients. Polymorph II when substantially crystallographically pure is for all practical purposes stabile.

Polymorph II can conveniently be prepared by recrystallizing the free base form of sabeluzole in a suitable solvent such as a lower alkanol such as ethanol, propanol or butanol, preferably isopropanol. Said recrystallization comprises dissolution of the free base form in the hot solvent, optional treatment with charcoal, filtration, re-heating to reflux temperature, cooling and seeding with the polymorph II. In order to obtain substantially crystallographically pure polymorph II, the seeding should be conducted at low temperature, in this case at or below 30° C. As the temperature of the seeded solution is allowed to cool further, polymorph II precipitates. Optionally said precipitation process may be sped up by additional cooling of the mixture or by the addition of a cosolvent such as water. The precipitate is filtered off, washed, dried and collected. Micronizing and sieving as described above yields microfine product.

PREPARATION EXAMPLE

Example 1

About 1 mole of sabeluzole was heated to reflux in about 0.8 l of isopropanol until all solid material was dissolved. The solution was filtered while hot and re-heated to reflux. The solution was then allowed to cool gradually to room temperature and when its temperature dropped below 30° C., the solution was seeded with previously obtained crystals of polymorph II. The reaction mixture was then allowed to cool further as substantially crystallographically pure polymorph II precipitated. The crystals were filtered off, washed, dried and collected; mp. 88.9° C.

Formulation Example

Example 2

In a fluidized bed granulator there were mixed until homogeneous 300 g of polymorph II of sabeluzole, 3.036 kg of lactose, 1.200 kg of corn starch and 150 g of Prejel PA5®. A spraying solution was prepared by pouring a solution of 9 g of sodium lanryl sulphate in 110 g of demineralized water into a stirred solution of 60 g of polyvinylpyrrolidine (PVP K90) in 1600 g of demineralized water. The thus obtained solution was sprayed on the granulate. The granulate was dried, sieved and then mixed with 1.200 kg microcrystalline cellulose and 30 g Aerosil® in a mixing apparatus. Subsequently, 60 g of magnesium stearate was added to the stirred mixtrue. The resulting product was compressed in a compression apparatus (Courtoy Excenterpers) to white, slightly vaulted bar tablets having a length of 10.5 mm, breadth of 5 mm and weight of 180 mg.

Clinical Examples

Example 3

A first open clinical trial on 9 patients with moderately advanced DAT showed stabilisation of all patients over the 6-month treatment period. Furthermore, three patients showed marked improvement with respect to recognizing relatives and remission of mutism.

Example 4

Subsequently, three multi-center, double-blind, placebo-controlled, parallel-group studies were done to assess the efficacy and safety of the treament of DAT with sabeluzole. The first was an international study, in which sabeluzole 5 mg b.i.d., sabeluzole 10 mg b.i.d. and placebo were compared over a 6-month treatment period. The statistical analysis of the total population (370 patients) failed to detect a difference between the 3 treatment groups on the total Alzheimer's Disease Assessment Scale (ADAS) cognitive, which was among the primary efficacy variables. However, further exploratory analyses yielded interesting results. In a subgroup, consisting of 170 patients out of 338 with 12 month data from those countries where deterioration of the placebo-group was detected, a significant difference in favor of sabeluzole was found between 5 mg b.i.d. and placebo for the total ADAS cognitive ($p=0.0096$) after 6 months treatment. This subgroup of countries was delineated after the over-all analysis of the first study had shown less deterioration than expected in the placebo group after 6 months as compared to the natural course of DAT. This was due to some, mostly non-English speaking countries, where stability or improvement in the placebo group was reported at 3 and 6 months, resulting in a significant treatment-country interaction ($p=0.0094$). There are several possible explanations for this. First, a trial effect on DAT—patients can be postulated in some countries. Second, diagnostic errors may have included patients with stable or reversible conditions. Third, the cognitive diagnostic Mini Mental State Exam (MMSE) and rating (ADAS) tools may have less validity in other languages than English.

Example 5

The second study consisted of part of the patients of first study continuing treatment for another 6 months under double-blind conditions (N=108). After 12-month treatment, a significant difference in favour of 5 mg sabeluzole b.i.d. as compared to placebo could be demonstrated on the sum of cognitive items ($p=0.03$) of ADAS with a positive trend on the total ADAS ($p=0.09$). The effect on the sum of cognitive items was due to consistent effects in the language domain: naming of objects ($p=0.04$), comprehension of spoken language ($p=0.008$), spoken language ability ($p=0.007$), word finding difficulty ($p=0.04$) and to a difference on constructional praxis ($p=0.03$). No effects on the memory tests were seen. Placebo patients deteriorated by 5 median points on the total ADAS cognitive, patients with 5 mg b.i.d. by 2.5 points. In the 10 mg b.i.d.-group, individual results were intermediate between those of the placebo and the 5 mg b.i.d.-group, but no statistical differences versus placebo could be shown. The first study indicated that sabeluzole treatment was well-tolerated and safe at the clinical, biochemical, hematological and ECG-level.

Example 6

A third clinical trial was a double-blind placebo-controlled 1-year trial (n=201 patients after 12 months) in probable Alzheimer patients with 2 different sabeluzole dosages (10 and 20 mg b.i.d.). Sabeluzole was shown to slow down deterioration at the 10 mg b.i.d. dose: in the observed case analysis for completers, a 0.04 significance was found between placebo and 10 mg bi.d. for the total ADAS cognitive. This significance came from a 0.018 p-value on the 9 cognitive items, whereas no effects were seen on the memory tests. The mean deterioration on the total ADAS cognitive was 5.7 points in the placebo group (which is in line with longitudinal data on the natural course of Alzheimer's disease) and 3.5 points for 10 mg b.i.d., 5.5 points for 20 mg b.i.d. The resuks came mainly from a clear effect in the moderate severity group with a MMSE of 14–21. Evaluation of responders (number of patients with $\leq 4$, $\leq 2.5$, $\leq 0$ increase on the ADAS) yielded similar results (62 vs. 42%, 48 vs. 33%, 34 vs. 26%, respectively for 10 mg b.i.d. and placebo). No effects were seen on the Clinical Global Impression (CGI) or the Geriatrics Evaluation by Relatives Rating Instrument (GERRI) scale. Sabeluzole was very well tolerated: the number of drop-outs caused by adverse experiences in the active 10 mg b.i.d. dose and placebo were similar. Only in the high 20 mg b.i.d. dose group were there somewhat more adverse events, which caused patients to drop-out.

In contrast to THA, indeed sabeluzole has no tolerance problem: whereas with THA 25% of the patients dropped-out because of abnormal Liver Function Tests (LFT) (values >3 times upper limit), only 7 patients (of whom 2 in the active 10 mg b.i.d. dose, 5 in the 20 mg b.i.d.) showed abnormal LFTs. In the first international trial (n=338 patients treated for 6 months) only one case with elevated LFTs was reported in the 10 mg b.i.d. group. All LFT-changes with sabeluzole were reversible and asymptomatic. In other trials, where patients have sometimes been treated and followed up for more than 4 years, no LFT abnormalities have been reported with sabeluzole.

Biochemical Example

Example 7

Human TR14 and IMR-32 neuroblastoma cells were cultured at high confluency in DMEM additioned with 0.015 HEPES, 1% FCS and 5 mg/ml gentamycin. The medium taken from these serum starved cells on consecutive days was used subsequently in assessing the survival fraction of TR14 cells incubated with these conditioned mediums. Tau-isolates from the serum-starved cells were obtained following art-known methods and were checked with SDS-polyacrylamide gel electrophoresis (PAGE). In all experiments, the Bio-Rad mini gel system with 75 mm gels was used. The SDS-gel was then blotted following the semi-drug blotting technique (Western Blotting) whereafter the immobilisation PDVF-membrane was blocked with a 5% (w/v) BSA solution in TBST. Immunodetection with AT-8 antibody and Tau-1 antibody showed a phosphatase-sensitive AT-8 immunoreactivity slightly shifted with regard to Tau-1 signal in tau-isolates from both cell types.

Subsequently, fresh TR 14 cells were incubated at low cell density with medium conditioned from serum-starved cells for a certain number of days and their survival fraction was assessed after 6 and 10 days in culture.

After 6 days of incubation, it was found that the cytotoxicity only became apparent when the TR 14 cells had been incubated with medium taken from serum-starved cells over 12 days or more. On the other hand, after 10 days in culture, the cytotoxic activity became apparent in the medium collected from 9 days of serum starvation. These observations show that there was a gradual release of a cytotoxic factor during serum starvation which conferred neurotoxicity with AT-8 expression on freshly seeded neuronal cells.

Freshly seeded IMR-32 cells after three days of incubation at low density with conditioned medium taken from 10-day serum-starved cells had a survival fraction of 63%±3%. As shown in the table below, addition of sabeluzole attenuated neurotoxicity in a narrow dose range (n=3 independent experiments).

| Sabeluzole | Survival fraction |
| --- | --- |
| 1 μM | 63 ± 5% |
| 0.5 μM | 61 ± 5% |
| 0.1 μM | 69 ± 3% |
| 0.01 μM | 66 ± 3% |

We claim:

1. A process of inducing in neuronal cells the expression of epitopes associated with aberrantly phosphorylated tau-protein, which method comprises contacting said cells with a medium conditioned from serum-starved cells for several days and having acquired cytotoxic activity.

* * * * *